United States Patent
Carr-Stock

[19]

[11] Patent Number: 6,165,148
[45] Date of Patent: Dec. 26, 2000

[54] WRIST/HAND/FINGER ORTHOSIS

[75] Inventor: Loretta M. Carr-Stock, 8585 The Meadows South, East Amherst, N.Y. 14051

[73] Assignee: Loretta M. Carr-Stock, East Amherst, N.Y.

[21] Appl. No.: 09/360,303

[22] Filed: Jul. 23, 1999

[51] Int. Cl.[7] .................................................... A61F 5/00
[52] U.S. Cl. ................................ 602/21; 602/5; 128/878; 128/879
[58] Field of Search .................................. 602/5, 20, 21, 602/22, 60, 61, 69; 128/877, 878, 879, 880; 473/61, 62

[56] References Cited

U.S. PATENT DOCUMENTS

| | | |
|---|---|---|
| D. 371,845 | 7/1996 | Varn . |
| 5,609,569 | 3/1997 | Offenhartz ................................ 602/61 |
| 5,637,078 | 6/1997 | Varn . |
| 5,733,249 | 3/1998 | Katzin et al. . |
| 5,766,142 | 6/1998 | Hess . |
| 5,772,620 | 6/1998 | Sziema et al. . |
| 5,782,784 | 7/1998 | Wassermann . |
| 5,848,979 | 12/1998 | Bonutti et al. . |

OTHER PUBLICATIONS

MMAR Medical Group, Houston, TX. Orthotic Product Catalog, Aug. 1, 1996.
Orthosis Corrective Systems, Inc., Pinellas Park, FL. Products Catalog, 1999.
Orthotic Rehabilitation Products, Inc., Tampa, FL. Product Catalog 1999–2000.
DeRoyal/LMB, Inc. Powell, TN. Product Catalog, 1997.

Primary Examiner—Kim M. Lewis
Attorney, Agent, or Firm—Simpson, Simpson & Snyder, L.L.P.

[57] ABSTRACT

A wrist/hand/finger orthosis comprises a pliable splint member elongated in a direction from forearm to fingertips, a cover enclosing the splint member, and a plurality of releasable straps connected to the cover. Proximal to distal, the splint member includes forearm, wrist, hand, and finger portions. A thumb peninsula extends from the hand portion of the splint member, and a circular cut out region is provided adjacent thereto for increasing pivotal freedom of the thumb peninsula. The straps have free ends which attach to respective attachment locations on the cover such that the straps cross over the patient's limb in diagonal or oblique orientation, and the strap attachment locations are preferably color-coded with the straps for ease of use.

13 Claims, 4 Drawing Sheets

WRIST/HAND/FINGER ORTHOSIS

BACKGROUND OF THE INVENTION

A. Field of the Invention

The present invention relates generally to the field of orthotic devices, and more particularly to an orthosis that supports a human wrist, hand and fingers in an anatomically correct position for treating patients with a variety of medical conditions, including CVA, multiple sclerosis, head trauma, dementia, Alzheimer's disease, Parkinson's disease, arthritis, and other debilitating conditions.

B. Description of the Prior Art

Prior art orthoses in the field of the present invention are known to include a pliable or moldable splint member, usually formed of metal, separated from skin by a padded cover for sake of comfort. A plurality of releasable straps are typically provided extending in a transverse direction normal to a longitudinal axis of the orthosis for securing the orthosis on the limb. There are several recognized disadvantages with regard to commercially available wrist/hand orthoses. One disadvantage is that the thumb support portion in prior art orthoses is not designed with the necessary degrees of freedom for proper thumb positioning, resulting in joint deformities and skin breakdown due to pressure points. Another disadvantage is that the straps do not evenly distribute pressure to the limb, do not address the points of flexion tone, and can promote a "tourniquet effect" around the wrist area due to their orthogonal relationship to the longitudinal axis of the orthosis and arm. A further disadvantage, particularly in prior art orthoses having three or more straps which are secured by hook-and-loop fastening means, is that the correct attachment location for the distal end of each strap can be difficult for the user or caretaker to find. Finally, it is recognized that orthoses of the prior art are not designed for optimal tendon and ligament positioning, a drawback that can lead to metacarpel (MCP) extension, wrist flexion, and thumb adduction deformities.

SUMMARY OF THE INVENTION

Accordingly, it is an object of the present invention to provide an improved wrist/hand/finger orthosis that overcomes the above-stated problems of the prior art, without sacrificing ease of manufacturing or reasonable cost of the end product. The orthosis described herein is designed to maintain optimal tendon and ligament position, thus preventing MCP extension and thumb adduction deformities induced by prior art splint designs.

A preferred embodiment of the present invention generally comprises a pliable splint member elongated in a direction from forearm to fingertips, a cover enclosing the splint member, and a plurality of releasable straps connected to the cover.

The splint member includes a forearm portion, a wrist portion, a hand portion, and a finger portion arranged in sequence along a longitudinal axis thereof, and a thumb peninsula extending from the hand portion. To increase pivotal freedom of the thumb peninsula relative to the rest of the splint member, a circular cut out region is provided in the hand portion adjacent the thumb peninsula.

The cover is made of washable fabric and includes a one-piece anterior side and a three-piece posterior side. The three pieces of the posterior side are arranged to define a central slit extending substantially the length of the cover and an end slit extending transversely across the cover, whereby the splint member can be inserted into and removed from the cover.

Four straps—namely a forearm strap, a wrist strap, a hand strap, and a finger strap—are provided for removably securing the orthosis in place. Each strap includes a first end fixedly attached to the cover and a second end provided with a hook-and-loop fastening patch (either a hook area or a loop area) intended to mate with an opposite hook-and-loop patch positioned at a predetermined respective attachment location on the posterior side of the cover. In accordance with a preferred form of the present invention, the attachment locations for the forearm strap, wrist strap, hand strap, and finger strap are positioned such that these straps cross the longitudinal axis of the splint member at an oblique angle thereto to secure the orthosis on the patient, thereby spreading pressure and preventing a tourniquet effect. The second ends of the straps are preferably color-coded to register with their respective attachment locations on the cover to facilitate proper securement of the orthosis.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
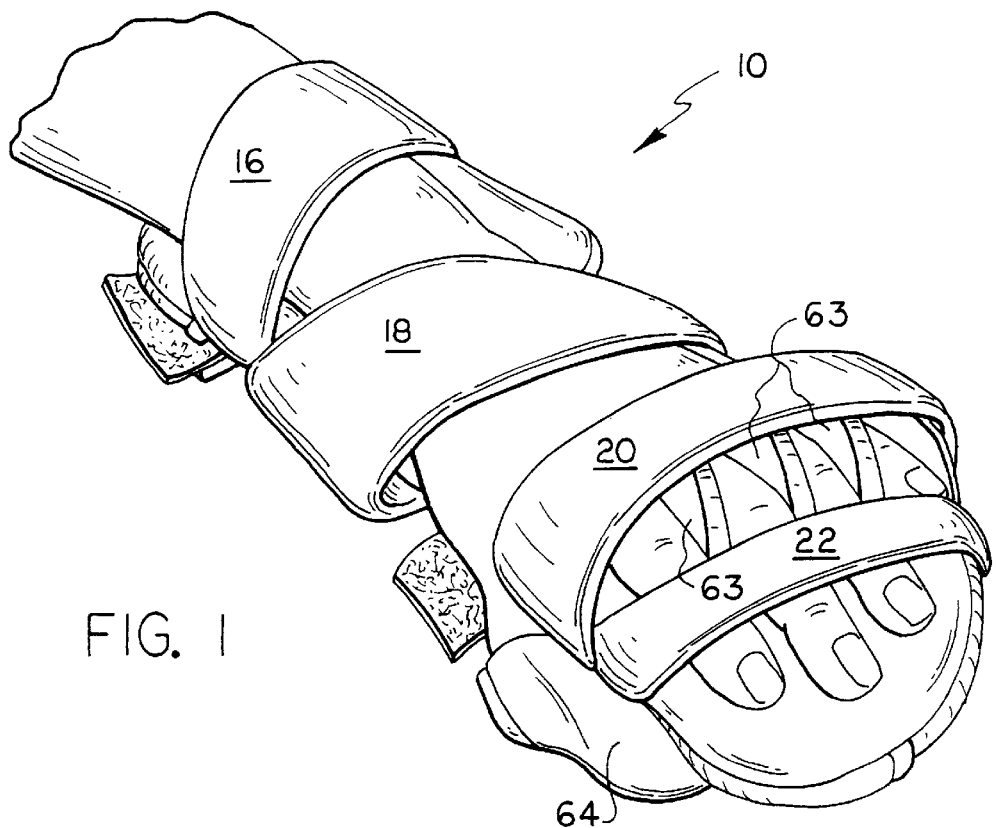
FIG. 1 is a top perspective view showing an orthosis formed in accordance with a preferred embodiment of the present invention as worn by a patient.
Figure 2:
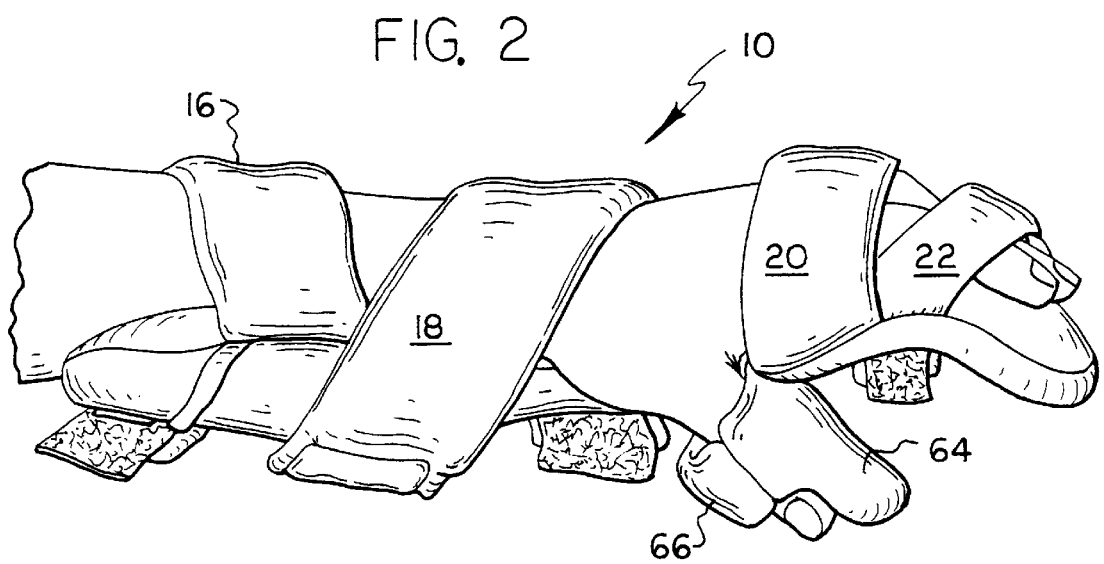
FIG. 2 is a side elevational view of the orthosis of the preferred embodiment as worn by a patient.
Figure 3:
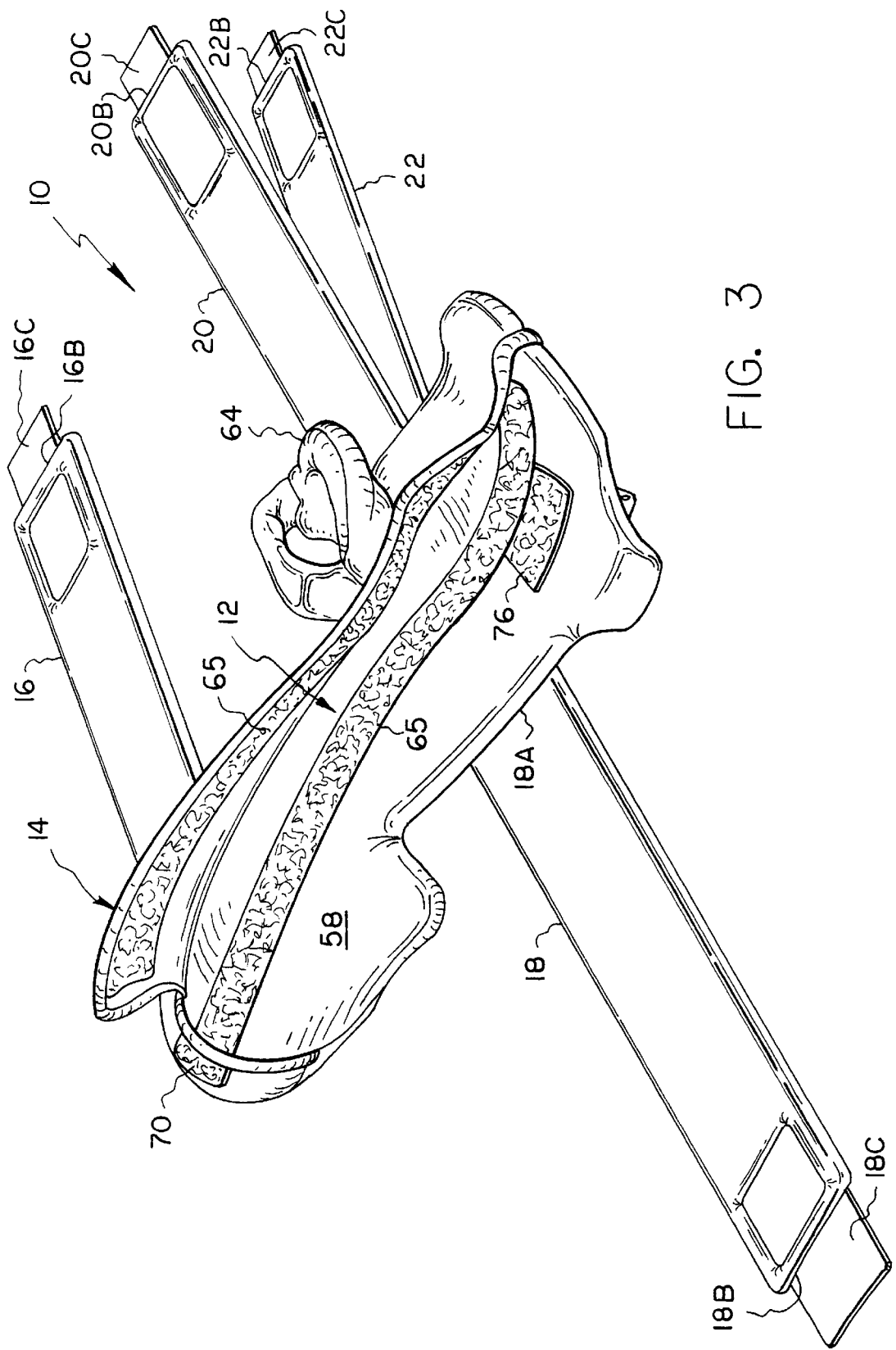
FIG. 3 is a bottom perspective view of the orthosis of the preferred embodiment intended to illustrate a removable cover thereof.

Initially reference is made to FIGS. 1–3 of the drawings, wherein a wrist/hand/finger orthosis formed in accordance with a preferred embodiment of the present invention is shown and identified generally by the reference numeral 10. Orthosis 10 is designed specifically for a left hand or a right hand, depending upon the involved limb. The drawings show only a left-hand orthosis, it being understood that a right-hand orthosis is constructed in a symmetrically opposite configuration. Orthosis 10 comprises a splint member 12 (FIG. 3), a cover 14 enclosing the splint member, and a plurality of straps 16, 18, 20, and 22 connected to the cover and arranged to run transversely across the splint member and over the patient's limb to removably secure the orthosis on the patient. Orthosis 10 may be constructed for custom fit, or in a plurality of standard sizes to fit a wide range of the patient population. Under proper fitting, a proximal end of orthosis 10 should reside more than halfway up the patient's forearm to decrease pressure on this area.

Figure 4:
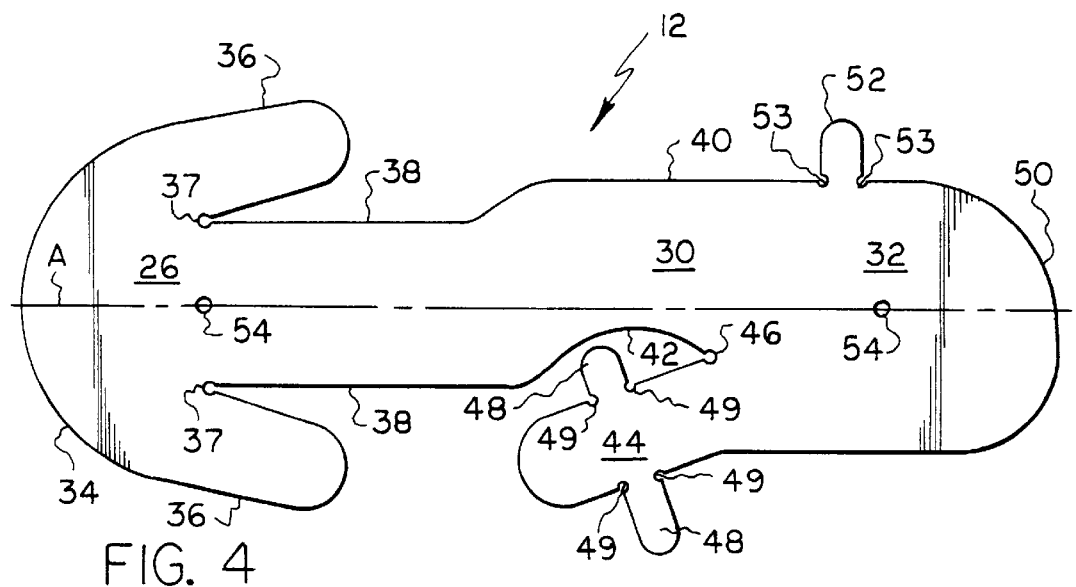
FIG. 4 is a top plan view of a splint member of the orthosis according to the preferred embodiment.

Splint member 12, shown in FIG. 4, is preferably formed of pliable sheet metal, such as 20 gauge steel (approximately 0.035 inches in thickness), so as to provide static support and enable selective bending of the splint member to any desired contour, thereby rendering the orthosis of the present invention useful for progressive static positioning therapy, range of motion therapy, and other treatments. Splint member 12 includes a forearm portion 26, a wrist portion 28, a hand portion 30, and a finger portion 32 arranged in adjacent sequence from proximal to distal along a longitudinal axis A of the splint member. Forearm portion 26 has an arcuate proximal edge 34 for promoting comfort and increasing flexion, tone, and spasticity. Forearm portion 26 also has a pair of side flaps 36 extending forwardly and outwardly of splint member 12; side flaps 36 can be bent upward to face each other to form a channel about the forearm, with small circular relief voids 37 being provided at the corner junctures where the side flaps merge with the splint member proper for improved bending performance. Wrist portion 28 extends from forearm portion 26 and is bounded by a pair of parallel side edges 38. Hand portion 30 includes a straight side edge 40, a concave side edge 42 defining a thenar cut-out on the thumb side of the palm to support the MCP joint and prevent it's subluxation, and a thumb peninsula 44 extending rearwardly and outwardly of splint member 12 alongside concave side edge 42. In order for thumb peninsula 44 to be positionable as dictated by changing treatment requirements, a circular cut-out region 46 is provided adjacent thumb peninsula 44 at its corner juncture with the remainder of splint member 12. Cut-out region 46 allows improved freedom in isolated turning and folding of thumb peninsula 44 medially, laterally, anteriorly, and posteriorly relative to the remainder of splint member 12 to accommodate thumb adduction, abduction, flexion, and joint deformities. Thumb peninsula 44, which is designed to extend the full length of the thumb to distribute pressure evenly, has a pair of opposite medial and lateral side wings 48 each bounded by a pair of relief cut-outs 49 that can be bent upward to face each other to form a channel restricting thumb movement at the IP joint. Finger portion 32 is bounded by a curvilinear distal edge 50, and includes an outwardly projecting tab 52 provided with adjacent relief cut-outs 53 so that it can be folded upward next to the fifth digit interphalangeal (IP) joint to prevent or treat ulnar deviation. A pair of dowel holes 54 near opposite ends of splint member 12 are used to locate the workpiece from which the splint member is cut or machined on a machine tool, band saw, or the like. Splint member 12 is curved through hand portion 30 and finger portion 32 to contour to the natural cascade of the patient's hand.

Figure 5:
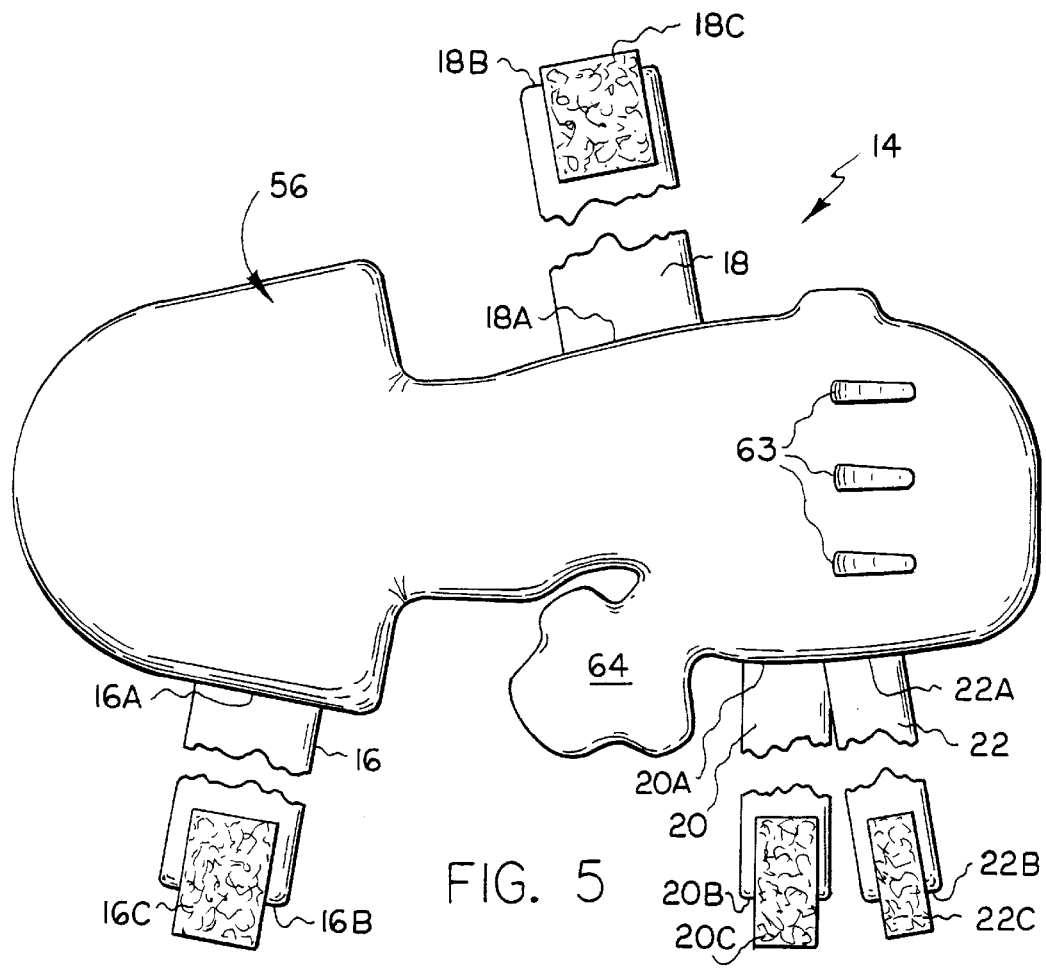
FIG. 5 is a top plan view of the cover of the orthosis according to the preferred embodiment.
Figure 6:
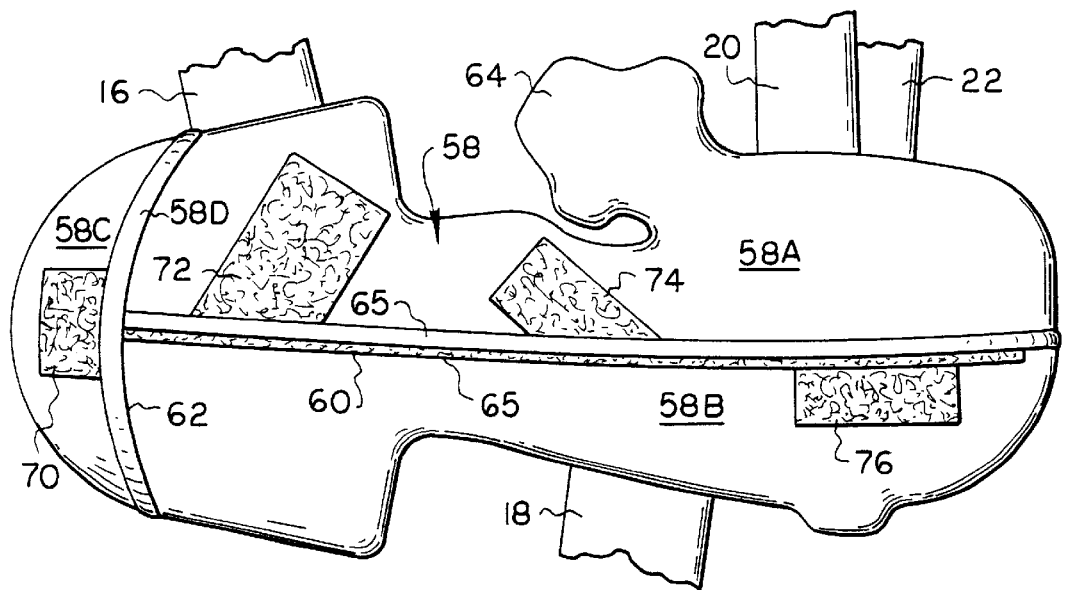
FIG. 6 is a bottom plan view thereof.
Figure 7:
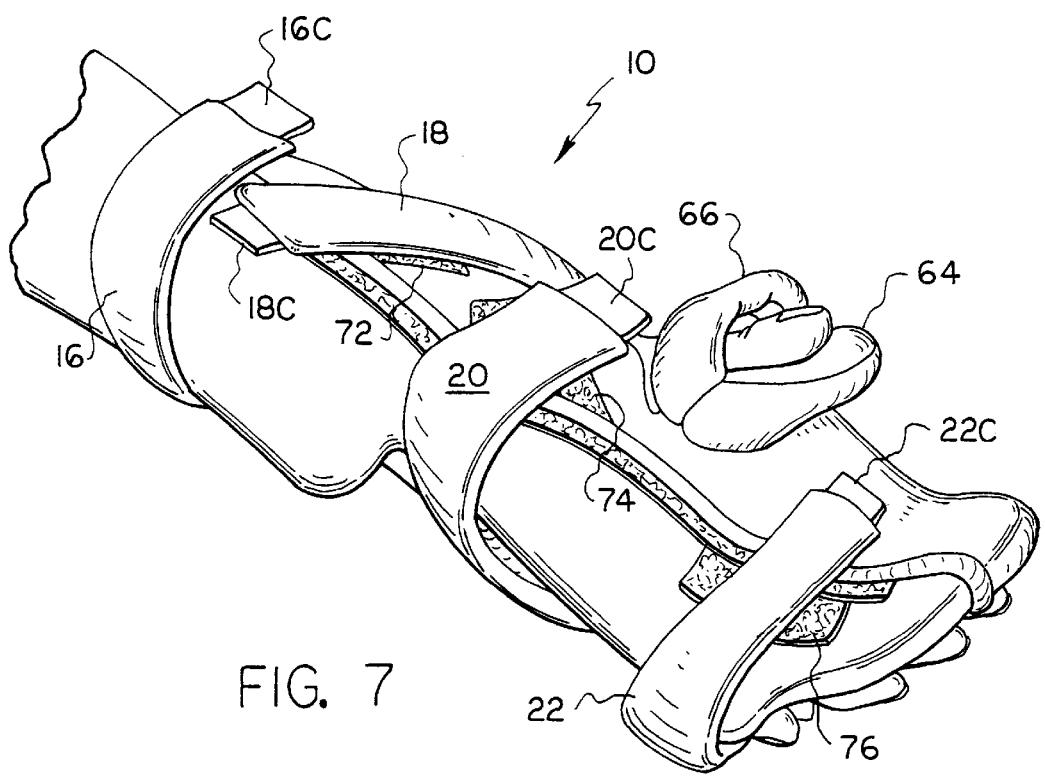
FIG. 7 is a bottom perspective view showing the orthosis of the preferred embodiment as worn by a patient.

Cover 14 will now be described by making reference primarily to FIGS. 5 and 6. Cover 14 is preferably formed from washable fabric that provides padding and wicks away moisture from the skin surface. Cover 14 is shaped to correspond generally with splint member 12 to fittingly enclose the splint member and includes an anterior side 56 of one-piece construction and a posterior side 58 of three-piece construction. Splint member 12 can be inserted into and removed from cover 14 by virtue of a central slit 60 through posterior side 58 extending substantially the length of cover 14, and an end slit 62 also through posterior side 58 at the proximal end of cover 14 that encloses forearm portion 26 of the splint member. Central slit 60 is defined by the side-by-side arrangement of fabric pieces 58A and 58B, while end slit 62 is defined by the overlapping, unattached distal edge 58D of fabric piece 58C. Hook-and-loop fastening strips 65 along central slit 60 permit releasable closure of the central slit. As an optional feature, three finger separators 63 project upwardly from anterior side 56 over finger portion 32. Finger separators 63 preferably have "shark fin" profile shape for easy manipulation and are open through posterior side 58 to enable insertion of a gel pac for improved comfort and correct spacing. A thumb pocket 64 is encloses thumb peninsula 44; due to the provision of wings 48 on thumb peninsula 44, the additional feature of a thumb strap 66 connected to thumb pocket 64, as shown in FIGS. 2, 3 and 7, is optional.

Cover 14 further includes four different strap attachment locations on posterior side 58, defined in the preferred embodiment by hook-and-loop patches 70, 72, 74, and 76 sewn or otherwise fastened on the posterior side. As will be described hereinbelow, hook-and-loop patches 70, 72, 74, and 76 are used to releasably attach straps 16, 18, 20, and 22, respectively, and can be either hook or loop in nature depending on the nature of a mating patch on the associated strap.

Four straps are provided for securing orthosis 10 on a patient's forearm and hand, specifically a forearm strap 16, a wrist strap 18, a hand strap 20, and a finger strap 22. Forearm strap 16, preferably 1½ inches wide, includes a first end 16A fixedly attached, such as by sewing, to cover 14 along the medial seam between anterior side 56 and posterior side 58 near third piece 58C, and a second end 16B provided with a hook-and-loop patch 16C for detachable connection to corresponding hook-and-loop patch 70 on posterior side 58. Hook-and-loop patch 70 is centrally located on third piece 58C adjacent unattached distal edge 58D, such that forearm strap 16 crosses over forearm portion 26 and the patient's forearm at a slightly oblique angle to longitudinal axis A, with hook-and-loop patch 16C being mated to corresponding hook-and-loop patch 70 for securement. Wrist strap 18, preferably 2 inches wide, includes a first end 18A fixedly attached to cover 14 along the lateral seam between anterior side 56 and posterior side 58 opposite thumb pocket 64, and a second end 18B having a hook-and-loop patch 18C for detachable connection to corresponding hook-and-loop patch 72 on posterior side 58. Hook-and-loop patch 72 is located on first piece 58A under forearm portion 26, whereby wrist strap 18 crosses over wrist portion 28 and the patient's wrist at an oblique angle to longitudinal axis A to bring hook-and-loop patch 18C into attachment with corresponding hook-and-loop patch 72. Hand strap 20 is preferably 1½ inches wide and includes a first end 20A fixedly attached to cover 14 along the medial seam between anterior side 56 and posterior side 58 just distally of thumb pocket 64 and a second end 20B.

Second end 20B includes a hook-and-loop patch 20C for detachable connection to associated hook-and-loop patch 74 located at an intermediate position along first piece 58A. Thus, hand strap 20 crosses over hand portion 28 and the patient's MCP joints at a slightly oblique angle to longitudinal axis A to engage hook-and-loop patch 20C with corresponding hook-and-loop patch 74. Finally, finger strap 22 is preferably 1¼ inches wide and includes a first end 22A fixedly attached to cover 14 along the medial seam between anterior side 56 and posterior side 58 in overlapping adjacency to first end 20A of hand strap 20. Finger strap 22 also has a second end 22B provided with a hook-and-loop patch 22C for detachable connection to corresponding hook-and-loop patch 76 on posterior side 58. Hook-and-loop patch 76 is located on second piece 58B under finger portion 32, such that finger strap 22 crosses over finger portion 32 and the patient's PIP joints at a slightly oblique angle to longitudinal axis A to join hook-and-loop patch 22C with corresponding hook-and-loop patch 76. Accordingly, the diagonal orientation of straps 16, 18, 20, and 22 in the presently described embodiment helps prevent discomfort by evenly distributing pressure along the limb.

A further aspect of orthosis 10 which makes the orthosis easy to don is color coding of straps 16, 18, 20, and 22 with their respective attachment locations on cover 14. According to a first color coding scheme, at least a portion of each strap, such as hook-and-loop patches 16C, 18C, 20C, and 22C, has a distinct color uniquely its own relative to the other straps, and the attachment locations defined by hook-and-loop patches 70, 72, 74, and 76 have the same color as their counterpart strap or strap portion. For example, under the first scheme, hook-and-loop patches 16C and 70 could be black, hook-and-loop patches 18C and 72 could be red, hook-and-loop patches 20C and 74 could be yellow, and hook-and-loop patches 22C and 76 could be white. According to a second color coding scheme, alternating colors are used to identify attachment locations for particular straps. For example, under the second scheme, hook-and-loop patches 16C and 70 could be black, hook-and-loop patches 18C and 72 could be white, hook-and-loop patches 20C and 74 could be black, and hook-and-loop patches 22C and 76 could be white.

As will be appreciated from the foregoing description, orthosis 10 of the present invention is suitable for long-term care patients, subacute patients, and acute rehabilitation patients and introduces improvements heretofore lacking in the field.

What is claimed is:

1. A wrist/hand/finger orthosis comprising:
   an elongated pliable splint member including a forearm support portion, a wrist support portion, a hand support portion, and a finger support portion respectively arranged in adjacent sequence along a longitudinal axis of said splint member and a thumb support peninsula extending from said hand support portion;
   a cover enclosing said splint member, said cover including a plurality of strap attachment locations; and
   a plurality of straps extending transversely across said support member, each of said plurality of straps including a first end fixed to said cover and a second end adapted for releasable attachment to a corresponding one of said plurality of strap attachment locations;
   wherein at least one of said plurality of straps crosses said longitudinal axis of said splint member at an oblique angle thereto when said second end of said at least one strap is attached to said corresponding one of said plurality of strap attachment locations.

2. The orthosis according to claim 1, wherein said plurality of straps comprises a forearm strap extending across said forearm support portion, a wrist strap extending across said wrist support portion, a hand strap extending across said wrist support portion of said support member, and a finger strap extending across said finger support portion, and said plurality of strap attachment locations comprises a forearm strap attachment location for receiving said second end of said forearm strap, a wrist strap attachment location for receiving said second end of said wrist strap, a hand strap attachment location for receiving said second end of said hand strap, and a finger strap attachment location for receiving said second end of said finger strap.

3. The orthosis according to claim 2, wherein said forearm strap crosses said longitudinal axis at an oblique angle thereto when said second end of said forearm strap is attached to said forearm strap attachment location.

4. The orthosis according to claim 2, wherein said wrist strap crosses said longitudinal axis at an oblique angle thereto when said second end of said wrist strap is attached to said wrist strap attachment location.

5. The orthosis according to claim 2, wherein said hand strap crosses said longitudinal axis at an oblique angle thereto when said second end of said hand strap is attached to said hand strap attachment location.

6. The orthosis according to claim 2, wherein said forearm strap, said wrist strap, and said hand strap cross said longitudinal axis at an oblique angle thereto when said second end of said forearm strap is attached to said forearm strap attachment location, said second end of said wrist strap is attached to said wrist strap attachment location, and said second end of said hand strap is attached to said hand strap attachment location.

7. The orthosis according to claim 6, wherein said forearm strap attachment location, said wrist strap attachment location, said hand strap attachment location, and said finger strap attachment location each have a color associated therewith, and said wrist strap, said hand strap, and said finger strap each include a color code corresponding to said color associated with a respective one of said attachment locations.

8. The orthosis according to claim 7, wherein said forearm strap includes a hook-and-loop fastening element of a first color at said second end thereof and said cover includes a hook-and-loop fastening element of said first color at said forearm strap attachment location, said wrist strap includes a hook-and-loop fastening element of a second color at said second end thereof and said cover includes a hook-and-loop fastening element of said second color at said wrist strap attachment location, said hand strap includes a hook-and-loop fastening element of a third color at said second end thereof and said cover includes a hook-and-loop fastening element of said third color at said hand strap attachment location, and said finger strap includes a hook-and-loop fastening element of a fourth color at said second end thereof and said cover includes a hook-and-loop fastening element of said fourth color at said finger strap attachment location.

9. The orthosis according to claim 8, wherein said first color and said third color are the same, said second color and said fourth color are the same, and said first color and said second color are different.

10. The orthosis according to claim 8, wherein said first color, said second color, said third color, and said fourth color are all different from each other.

11. The orthosis according to claim 2, wherein said first end of said hand strap and said first end of said finger strap are at least partially overlapping one another.

12. A wrist/hand/finger orthosis comprising:
   an elongated pliable splint member including a forearm support portion, a wrist support portion, a hand support portion, and a finger support portion respectively arranged in adjacent sequence along a longitudinal axis of said splint member and a thumb support peninsula extending from said hand support portion and bendably pivotal relative thereto;
   a cover enclosing said splint member; and
   a plurality of straps releasably attachable to said cover;
   wherein said hand support portion includes a thenar cut out region adjacent said thumb support peninsula for increasing pivotal freedom of said thumb support peninsula relative to said hand support portion.

13. The orthosis according to claim 12, wherein said thumb peninsula includes a pair of opposite sides, each of said opposite sides having a wing extending therefrom, whereby a channel for a thumb may be formed by bending said wings.

* * * * *